United States Patent [19]

Lindemann et al.

[11] 4,233,19:
[45] Nov. 11, 198(

[54] DETERGENT COMPOSITIONS

[75] Inventors: Martin K. O. Lindemann, Bridgewater; Robert J. Verdicchio, Succasunna, both of N.J.

[73] Assignee: Johnson & Johnson, New Brunswick, N.J.

[21] Appl. No.: 965,463

[22] Filed: Nov. 30, 1978

[51] Int. Cl.$^2$ .................. C11D 3/36; C11D 7/36
[52] U.S. Cl. .................. 252/545; 252/526; 252/546; 252/DIG. 7; 252/DIG. 13; 424/70; 260/924; 260/925
[58] Field of Search ......... 252/545, 546, 526, DIG. 7, 252/DIG. 13; 260/924–925; 424/70

[56] References Cited

U.S. PATENT DOCUMENTS

| | | | |
|---|---|---|---|
| 2,999,069 | 9/1961 | Masci et al. | 252/54 |
| 3,055,836 | 9/1962 | Masci et al. | 252/54 |
| 3,928,251 | 12/1975 | Bolich, Jr. et al. | 252/54 |
| 3,950,417 | 4/1976 | Verdicchio et al. | 252/54 |

*Primary Examiner*—Mayer Weinblatt
*Attorney, Agent, or Firm*—Steven P. Berman

[57] ABSTRACT

An improved cleansing, foaming and nonirritating detergent and cleansing composition for personal care use is provided containing phosphobetaine surfactant or phosphitaine surfactant as an active ingredient.

10 Claims, No Drawings

DETERGENT COMPOSITIONS

BACKGROUND OF THE INVENTION

The present invention relates to detergent and cleansing compositions, and more particularly to those detergent and cleansing compositions which have relatively low ocular irritation and yet exhibit good foam volume and improved foam stability.

Detergent and cleansing compositions, like most types of cleaning agents, generally comprise a mixture of one or more surfactants as the active ingredient, as well as builders, perfumes, coloring agents, thickeners, and the like. The surfactant molecules have two or more different moieties comprising: (1) a hydrophobic hydrocarbon chain miscible with organic materials and (2) a hydrophilic moiety miscible with water. Surfactants of this type solubilize fat soluble soils via a complex adsorption/emulsification mechanism. This process allows the efficient removal of soil from the body. The surfactants may be classified as anionic, cationic, nonionic or amphoteric depending upon the nature of the hydrophile.

It is desirable that detergent and cleansing compositions have good foam volume and good foam stability, particularly if they are to be used as shampoos. The amount of foam generated by a shampoo composition has a direct bearing on the perceived efficiency with which it cleans the hair. The stability of the foam generated provides an indication to the user as to how long it will keep the hair lathered. Generally speaking, the greater the volume of foam produced and the more stable the foam, the more efficient the perceived cleansing action of the shampoo. In addition, other detergent and cleansing compositions, such as liquid skin cleansers and baby bath compositions, are enhanced by high foam volume and good foam stability.

Furthermore, it is essential that products of this type and in particular a shampoo recommended for use on infants and/or children have low ocular irritation and sting potential.

In the prior art, attempts to achieve such low ocular irritating compositions have been described such as by Masci et al. in U.S. Pat. No. 3,055,836 and Bolich et al. in U.S. Pat. No. 3,928,251. Such compositions have contained either an amphoteric/anionic reaction product or a betaine/sultaine-anionic blend in combination with ethoxylated nonionics but such formulations, however, have generally exhibited inferior foam volume and stability when compared to traditional shampoo formulations.

It has now been discovered that the aforementioned deficiencies are readily and unexpectedly overcome while maintaining a low level of ocular irritancy by using a novel class of amphoteric and zwitterionic betaine surfactants, so-called "phosphobetaines" and "phosphitaines", alone or in combination with other surfactants. These phosphobetaines and phosphitaines are amphoteric and zwitterionic surfactants having at least one phosphorous-containing anion in the molecule as described in co-pending U.S. patent application Ser. No. 965,461, filed Nov. 30, 1978, and Ser. No. 965,462, filed Nov. 30, 1978.

It is thus an object of the present invention to prepare detergent and cleanser compositions which are effective for personal cleansing of the skin and hair.

It is another object of the present invention to provide detergent and cleansing compositions which provide good foam volume and good foam stability.

It is yet a further object of the present invention to provide detergent and cleansing compositions which, while being effective cleansing agents for the skin and hair, exhibit low irritancy.

These and other objects of the present invention will become apparent to one skilled in the art from the detailed description given hereinafter.

SUMMARY OF THE INVENTION

This invention encompasses detergent and cleansing compositions comprising as the active ingredient a phosphobetaine surfactant, and preferably at least one other surfactant selected from the group consisting of anionic, nonionic, cationic and amphoteric detergents. The balance of the compositions can comprise various detergency and cleansing adjuncts, fillers, carriers and the like well known in the art.

DETAILED DESCRIPTION OF THE INVENTION

The detergent and cleansing compositions of the present invention comprise as the active ingredient a phosphobetaine and preferably at least one other surfactant.

The phosphobetaines and phosphitaines which are useful in the present invention are novel compounds described and claimed in copending patent applications Ser. Nos. 965,461 and 965,462 filed Nov. 30, 1978 and Nov. 30, 1978, respectively, and are characterized at amphoteric and zwitterionic betaine compounds having at least one phosphorous-containing anion in the molecule.

The phosphobetaines are of the formula

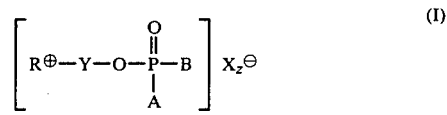

wherein
A is selected from O$^-$, OM and —O—Y—R$^\oplus$
B is selected from O$^-$ and OM'
X$^\ominus$ is an anion
z is an integer from 0 to 2
with the proviso that only one of A and B can be O$^-$ and z is of a value necessary for charge balance (i.e., when A and B are O$^-$ and OM', or OM and O$^-$, respectively, z is 0; when A and B are OM and OM', or —O—Y—R$^\oplus$ and O$^-$, respectively, z is 1; when A is —O—Y—R$^\oplus$ and B is OM', z is (2);

R is an amidoamine reactant moiety of the formula

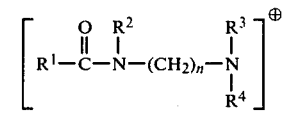

wherein
R$^1$ is alkyl, alkenyl, alkoxy, or hydroxyalkyl of from 5 to 22 carbon atoms each, or aryl or alkaryl of up to 20 carbon atoms;
R$^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms;

$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12;

The term "polyoxyalkalene radical" as used above in the definition of $R^2$, $R^3$ and $R^4$ may be of the formula $(R^5-O-R^{5'})_m$, wherein $R^5$ and $R^{5'}$ are alkyl of from 1 to 4 carbon atoms and m is an integer from about 2 to 10.

In addition to the foregoing definitions wherein R is amidoamine, R may be an N-heterocyclic radical which may contain one additional hetero atom (e.g., oxygen sulfur or another nitrogen) and contains 5 to 6 total ring carbon atoms; optionally said heterocyclic radical may be substituted with alkyl and/or hydroxyalkyl of up to 20 carbon atoms each. Typical of such N-heterocyclic radicals are imidazolyl, N-alkylmorpholino, alkylpyrimidino, alkyloxazolinyl, and the like. Such compounds may be represented by the formula

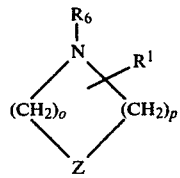

wherein
Z is N, S or O;
o is an integer from 0 to 3;
p is an integer from 1 to 3;
provided that the sum of o+p is from 3 to 4;

$R^1$ is defined as before and is linked to a ring carbon atom; and $R_6$ is alkyl of from 2 to 6 carbon atoms which may be substituted with a hydroxyl group at the terminal or a non-terminal carbon atom;

Y may be alkylene, optionally interrupted by up to 3 oxygen atoms, of up to 12 carbon atoms, which alkylene chain may optionally be substituted with loweralkyl, alkoxy, hydroxy or hydroxyalkyl, e.g., of no more than 10 carbon atoms each.

M and M', which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals (e.g., sodium or potassium), alkaline earth metals (e.g., magnesium or calcium), and mono-, di-, or triethanolamine. With reference to formula (I) above, wherein both M and M' are contained, there is the proviso that when either M or M' is an organic radical (b), the other of M and M' must be hydrogen or a salt radical (c).

The phosphitaines are of the formula

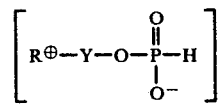

wherein R and Y are as defined above.

The phosphobetaine compounds and phosphitaine compounds described above can be prepared in accordance with the processes described in copending applications Ser. Nos. 965,461 and 965,462, filed Nov. 30, 1978 and Nov. 30, 1978, respectively, the teachings of which are incorporated herein by reference.

Representative phosphobetaine and phosphitaine compounds useful in the present invention include compounds having the following structures:

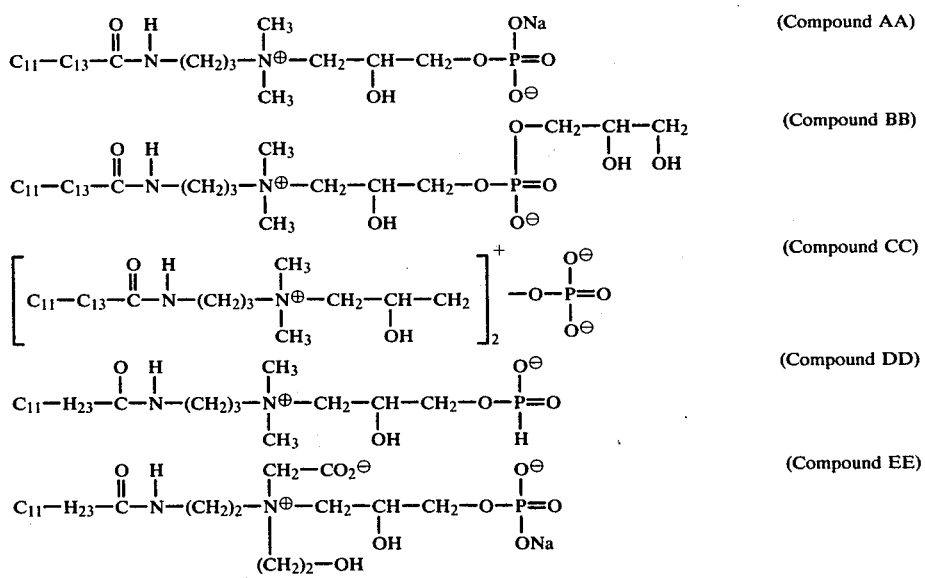

The phosphobetaine and phosphitaine compounds can be present in the detergent and cleansing compositions of the present invention in a range of from about 1 to 20% by weight of the total composition.

Preferred embodiments of the present invention relate to detergent and cleansing compositions containing a phosphobetaine or a phosphitaine and at least one other surfactant selected from the group consisting of amphoteric, nonionic, anionic and cationic detergents.

The amphoteric surfactants which may be used in the present invention include betaines, sultaines and n-alkylamino propionates and n-alkylimino dipropionates. The betaine and sultaine surfactants useful in this invention are described in U.S. Pat. No. 3,950,417 issued Apr. 13, 1976, which is incorporated herein by reference and the n-alkylamino propionates and n-alkylimino dipropionates are sold under the tradename Deriphats by General Mills.

The preferred betaine amphoteric surfactants include the alkylbetaines such as cocodimethylcarboxymethylbetaine, lauryldimethylcarboxymethylbetaine, lauryldimethyl-alpha-carboxyethylbetaine, cetyldimethylcarboxymethylbetaine, lauryl-bis-(2-hydroxyethyl) carboxymethylbetaine, oleyldimethyl-gamma-carboxypropylbetaine, lauryl-bis-(2-hydroxypropyl) alpha-carboxyethylbetaine, and the like; the sultaines such as cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidodimethylpropylsultaine, laurylamido-bis-(2-hydroxyethyl) propylsultaine, and the like. The preferred n-alkylamino propionates and n-alkylimino dipropionates include those of the following structures:

$$R-N^{\oplus}H_2-CH_2-CH_2-COO^{\ominus}$$

and

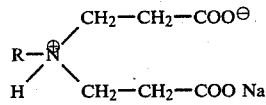

wherein R is from about 8 to 22 carbon atoms and mixtures thereof. The amphoteric detergents should be present in an amount from about 1 to 20% by weight of the total composition.

It is envisioned that any anionic surfactant may be used in the compositions of the invention such as, for example, an alkyl sulfate of the formula $R-CH_2-OSO_3X$, an alkylether sulfate of the formula $R(OCH_2CH_2)_p-OSO_3X$, an alkylmonoglyceryl ether sulfonate of the formula

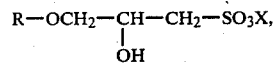

an alkylmonoglyceride sulfate of the formula

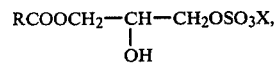

an alkylmonoglyceride sulfonate of the formula

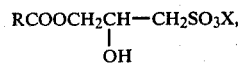

an alkyl sulfonate of the formula $RSO_3X$, an alkylaryl sulfonate of the formula

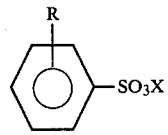

an alkyl sulfosuccinate of the formula

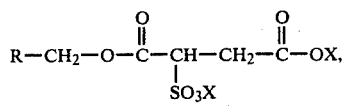

an alkyl sarcosinate of the formula

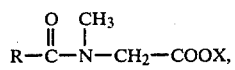

an acyl isothionate of the formula

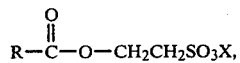

an alkyl methyl tauride of the formula

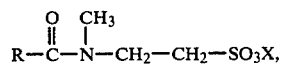

a fatty acid protein condensate of the formula

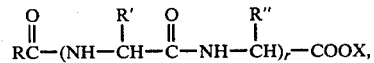

an alcohol ether carboxylate of the formula $RO(CH_2CH_2O)_q-CH_2CO_2X$ and the like; wherein R is higher alkyl having from 7 to 17 carbon atoms; R' and R" are members each selected from the group consisting of hydrogen, loweralkyl, hydroxyloweralkyl, thioloweralkyl, carboxyloweralkyl, aminoloweralkyl, benzyl, and p-hydroxybenzyl; X is a member selected from the group consisting of alkali metal ions, alkaline earth metal ions, ammonium ions, and ammonium ions substituted with from 1 to 3 loweralkyls; p is an integer from about 3 to about 6; q is an integer from 2 to about 6 and r is an integer from 2 to 10.

The preferred type of anionic surfactant is an alkyl ether sulfate, more preferably sodium tridecyl-alcohol ether sulfate in which p is 1 to 5. The anionic detergent should be present in an amount of from about 1 to 20% by weight of the total composition.

Nonionic detergents which are useful include the alkylene oxide ethers of phenols, fatty alcohols, and alkyl mercaptans; the alkylene oxide esters of fatty acid amides; the condensation products of ethylene oxide with partial fatty acid esters, and mixtures thereof. The polyoxyalkylene chain in such agents may contain from 5 to 100 alkylene oxide units in which each alkylene unit has from 2 to 3 carbon atoms.

The preferred nonionic surfactant in the compositions of the invention is a water-soluble polyoxyethylene derivative of a hydrophobic base, said derivative being a member of the group consisting of the reaction products of 9–20 carbon atom fatty acid monoesters of aliphatic polyhydric alcohols, which polyhydric alcohols contain at least 3 hydroxyls, with at least 10 moles of ethylene oxide, and preferably with from about 10 to about 100 moles of ethylene oxide.

The nonionic surfactant should be present in an amount of from about 1 to 20% by weight of the total composition.

Cationic surfactants suitable in these compositions include mono- and bis-quaternary ammonium halides such as stearyldimethylbenzylammonium chloride, cetyltrimethylammonium chloride, N,N-dioctadecyl-N,N,N',N'-tetramethyl-1,5 (3 oxapentylene)diammonium dibromide; tertiary amine salts such as cocamidopropyldimethylamine hydrochloride stearylamidopropyldimethylamine citrate; cationic polymers such as hydroxyethyl cellulose reacted with epichlorohydrin and then quaternized with trimethylamine. (Polymers of this type are sold by Union Carbide under the tradename Polymer JR.) The cationic surfactants should be present in an amount of from about 1 to 5% by weight of the total composition.

The total amount of the active surfactant ingredients in the present invention should not be greater than about 35% by weight of the total composition in order to avoid ocular irritation problems, preferably from about 8 to 15% by weight of the total composition.

In addition, other ingredients conventionally added to detergent and cleansing compositions for personal use, such as dyes, preservatives, perfumes, thickeners, opacifiers, conditioners, emollients, buffering agents, and the like, may be added in minor amounts. Ingredients such as dyes, preservatives and perfumes together usually constitute less than 2% by weight of the total composition and thickeners may be added to the composition in an amount of from about 1 to about 3% by weight of the total composition.

The detergent and cleansing compositions of the present invention may be concentrate compositions which are subsequently modified by dilution with water or other diluents to provide the ultimate compositions for use or they may be the ultimate cleansing compositions to be employed without modification. The compositions of the present invention are primarily useful in shampoo formulations where high foaming characteristics as well as low ocular and skin irritation potential are desired. They may also be used as liquid soaps and cleansers such as baby bath compositions, in bubble bath compositions, as well as in compositions suitable for cleansing animals and inanimate objects.

The aforementioned detergent and cleansing compositions are prepared by admixing the phosphobetaine or phosphitaine with the other surfactant(s), if utilized, at room temperature or slightly elevated temperatures (about 50° C.) and then sufficient deionized water is added to bring the composition to about three-quarters of its intended weight. The pH is adjusted to within the range of 5 to 8, preferably 6 to 8, by adding strong acid, e.g., HCL, or strong base, e.g., NaOH, as needed. Other ingredients such as viscosity builders, preservatives, dyes, perfumes and the like are incorporated prior to adjusting the pH and adding the remainder of the water.

The detergent and cleansing compositions of the present invention can be tested for ocular irritation by the following modified Draize Test (J. H. Draize et al., Toilet Goods Assn. No. 17, May 1952, No. 1. Proc. Sci. Sect.).

A 0.1 ml sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

The detergent and cleansing compositions of the invention provide high foam volume and moreover outstanding foam stability as measured by an adaption of the well-known Ross-Miles foam test principle ["Oil and Soap" 18.99–102 (1941)]:

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin-dioxane solution, which is stored in an amber bottle, should be prepared fresh on the day that the tests are run.

The composition to be tested is diluted by adding 376 cc. of distilled water to 4 grams of the composition, and then by adding 20 cc. of the lanolin-dioxane solution described above while mixing. Heat is produced when the lanolin-dioxane solution is added to the solution of the composition in water and care must be taken in adjusting the temperature of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the detergent and cleansing compositions prepared in accordance with the present invention are illustrated by the following represetative examples. It will be understood, however, that the invention is not confined to the specific limitations set forth in the individual examples, but rather to the scope of the appended claims.

EXAMPLE I

A detergent and cleansing composition is prepared by charging 192.6 grams of a 35% active solution of Compound AA to a steam jacketed vessel with agitation. 225.0 grams of a 30% active solution of a cocamido betaine of the formula

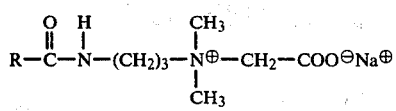

(R is a mixture of $C_{10}-C_{18}$)
is added with agitation followed by the addition of 200.0 grams of a 72% active solution of polyoxyethylene (80) sorbitan monolaurate and 50.0 grams of a 40% active solution of triethanolamine lauryl sulfate resulting in a clear, homogenous solution. 100.0 grams of deionized water is added and the mixture is heated to 60° C. and 10.0 grams of polyethylene glycol 6000 distearate are added with agitation over a period of 20 minutes or until the solution is clear. 100.0 grams of deionized water are added and 6.72 grams of 15% HCL to attain a pH of 7.0±0.1. 0.5 grams of Dowicil 200 preservative and 1.0 gram of benzyl alcohol are added followed by the addition of 25.0 grams of propylene glycol and 3.0 grams of fragrance. Sufficient deionized water is then added to produce 1000 grams (1 liter) of the desired composition consisting of the following ingredients:

|  | wt./wt. % |
|---|---|
| Compound AA | 6.0 |
| cocoamidobetaine | 6.0 |
| triethanolamine lauryl sulfate | 2.0 |
| propylene glycol | 2.5 |
| polyethylene glycol 6000 distearate | 1.0 |
| polyoxyethylene (80) sorbitan monolaurate | 15.0 |
| Dowicil 200 (Dow Chemical Company's tradename for the cis isomer of 1-(3-chloroalkyl)-3,5,7-triaza-1-azoneaadamantine chloride) | .05 |
| benzyl alcohol | .10 |
| dye and fragrance | .35 |
| deionized water | q.s. to 100% |
| pH = 7.0 with dilute HCL. | |

The above composition is tested for ocular irritation in accordance with the previously described modified Draize test and found to be a slight irritant.

The above composition is tested for foam volume and stability in accordance with the previously described modified Ross-Miles test and compared to two detergent compositions (Composition A and Composition B) prepared in accordance with the prior art teachings of U.S. Pat. Nos. 3,055,836 and 3,978,251 and yielded the following results as shown in Table I:

TABLE I

|  | Foam Volume (MM) | % Decay |
|---|---|---|
| Composition of Example I | 205 | 15 |
| Composition A | 100 | 90 |
| Composition B | 130 | 60 |

As can be readily seen from the results above, the detergent and cleansing composition prepared in accordance with the teachings of this invention possesses significantly higher foam volume and significantly superior foam stability when compared with compositions taught in the prior art.

EXAMPLES II–IV

The following compositions are prepared in accordance with the procedure of EXAMPLE I:

| | % wt./wt. EXAMPLE | | |
|---|---|---|---|
| | II | III | IV |
| Compound EE | 9.990 | — | — |
| Compound BB | — | 3.200 | — |
| Compound AA | — | — | 5.960 |
| sodium lauryl (3) ether sulfate | — | 6.216 | — |
| sodium lauryl sulfate | — | — | 3.332 |
| polyoxyethylene (80) sorbitan monococoate | — | 15.400 | 11.550 |
| polyethylene glycol 6000 distearate | 2.500 | — | 1.000 |
| 15% HCL | 1.400 | — | 1.600 |
| 10% NaOH | — | 5.600 | — |
| Dowicil 200 | 0.100 | 0.050 | 0.100 |
| dye | 0.001 | 0.002 | 0.003 |
| fragrance | 0.350 | 0.200 | 0.100 |
| deionized water | q.s. to 100% | q.s. to 100% | q.s. to 100% |

Each of the above compositions is tested for ocular irritations in accordance with the previously described modified Draize test and found to be a slight irritant.

Each of the above compositions (EXAMPLES II–IV) are tested for foam volume and stability in accordance with the previously described modified Ross-Miles test and the results are shown below in Table II:

TABLE II

| Composition | Foam Volume (MM) | % Decay |
|---|---|---|
| EXAMPLE II | 145 | 38 |
| EXAMPLE III | 130 | 9 |
| EXAMPLE IV | 125 | 6 |

As can be seen from the results in Table II, the detergent and cleansing compositions of EXAMPLES II–IV, each prepared in accordance with the teachings of the present invention, each possess good foam volume and excellent foam stability.

EXAMPLE V

A liquid detergent and cleansing composition consisting of the following ingredients is prepared in accordance with the teachings of EXAMPLE I:

|  | wt./wt. % |
|---|---|
| Compound AA | 5.0 |
| tridecyl alcohol ether (4) sulfate (TDES$_4$) | 15.0 |
| deionized water | 80.0 |
|  | 100.0 |
| pH adjusted to 7.0 with 10% HCL. | |

This composition exhibits low irritation and excellent foam properties.

EXAMPLE VI

A liquid detergent and cleansing composition consisting of the following ingredients is prepared in accordance with the teachings of Example I:

|  | wt./wt. % |
|---|---|
| Compound AA | 2.5 |
| $C_{14}-C_{16}$ α-olefin sodium sulfonate | 2.5 |
| dye | .01 |
| Dowicil 200 | .1 |
| fragrance | .2 |
| deionized water | q.s. to 100% |

EXAMPLE VII

A liquid detergent and cleansing composition consisting of the following ingredients is prepared in accordance with the teachings of EXAMPLE I:

| | wt./wt. % |
|---|---|
| Compound BB | 15.0 |
| sodium lauryl ether (3) sulfate | 15.0 |
| Polymer JR 400 | 1.0 |
| Dowicil 200 | .1 |
| fragrance | .3 |
| deionized water | q.s. to 100% |
| pH adjusted to 5.0 with citric acid. | |

This composition exhibits low irritation and excellent foam properties.

EXAMPLE VIII

A liquid detergent and cleansing composition consisting of the following ingredients is prepared in accordance with the teachings of EXAMPLE I:

| | wt./wt. % |
|---|---|
| Compound CC | 5.0 |
| lauryl amido propylbetaine | 5.0 |
| tridecyl ether sulfate | 5.0 |
| isoproponal | .5 |
| propylene glycol | 2.0 |
| dye | .01 |
| fragrance | .7 |
| deionized water | q.s. to 100% |
| pH adjusted to 7.5 with 10% HCL. | |

This composition exhibits low irritation and excellent foam properties.

EXAMPLE IX

A liquid detergent and cleansing composition consisting of the following ingredients is prepared in accordance with the teachings of EXAMPLE I:

| | wt./wt. % |
|---|---|
| Compound AA | 2.5 |
| Compound CC | 2.5 |
| polyoxyethylene (80) sorbitan monococoate | 5.0 |
| tridecyl ether sulfate | 5.0 |
| deionized water | q.s. to 100% |
| pH adjusted yo 7.0 with H$_2$SO$_4$ (dilute) | |

This composition exhibits low irritation and excellent foam properties.

EXAMPLE X

A liquid detergent and cleansing composition consisting of the following ingredients is prepared in accordance with the teachings of EXAMPLE I:

| | wt./wt. % |
|---|---|
| Compound DD | 5.0 |
| lauric-myristic-β-aminopropionic acid | 5.0 |
| sodium lauryl (3) ether sulfate | 10.0 |
| Dowicil 200 | .5 |
| deionized water | q.s. to 100% |
| pH adjusted to 6.5 with phosphoric acid | |

This composition exhibits low irritation and excellent foam properties.

EXAMPLE XI

A liquid detergent and cleansing composition consisting of the following ingredients is prepared in accordance with the teachings of EXAMPLE I:

| | wt./wt. % |
|---|---|
| Compound DD | 5.0 |
| 3-(N,N dimethyl-N-lauryl amino)-2-(hydroxyl propane sulfonate) | 5.0 |
| cetyl trimethylammonium chloride | 1.0 |
| deionized water | q.s. to 100% |
| pH adjusted to 5.0 with dilute HCL. | |

This composition exhibits low irritation and excellent foam properties.

EXAMPLE XII

A liquid detergent and cleansing composition consisting of the following ingredients is prepared in accordance with the teachings of EXAMPLE I:

| | wt.wt. % |
|---|---|
| Compound DD | 2.0 |
| sodium lauryl ether sulfate | 16.0 |
| lauric/myristic alkanolamide | 4.0 |
| deionized water | q.s. to 100% |
| pH adjusted to 7.5 | |

This composition exhibits low irritation and excellent foam properties.

EXAMPLE XIII

A liquid detergent and cleansing composition consisting of the following ingredients is prepared in accordance with the teachings of EXAMPLE I:

| | wt./wt. % |
|---|---|
| Compound EE | 5.0 |
| ethyleneoxylethylene-bis-(dimethyl-octadecylammonium chloride) | 2.0 |
| tridecyl ether sulfate | 10.0 |
| alcohol (SDA 40) | 1.0 |
| dye and fragrance | .35 |
| deionized water | q.s. to 100% |
| pH adjusted to 8.0 | |

This composition exhibits low irritation and excellent foam properties.

EXAMPLE XIV

A liquid detergent and cleansing composition consisting of the following ingredients is prepared in accordance with the teachings of EXAMPLE I:

| | wt./wt. % |
|---|---|
| Compound EE | 10.0 |
| dye and fragrance | .35 |
| Dowicil 200 | .05 |
| deionized water | q.s. to 100% |

This composition exhibits low irritation and excellent foam properties.

EXAMPLE XV

A liquid detergent and cleansing composition consisting of the following ingredients is prepared in accordance with the teachings of EXAMPLE I:

| | wt./wt. % |
|---|---|
| Compound BB | 5.0 |
| amidosultaine | 5.0 |
| polyoxyethylene (80) sorbitan monolaurate | 10.0 |
| preservative | .1 |
| dye and fragrance | .75 |
| deionized water | q.s. to 100% |

This composition exhibits low irritation and excellent foam properties.

EXAMPLE XVI

A liquid baby bath composition is prepared having the following formulation:

| | wt./wt. % |
|---|---|
| Compound EE | 2.50 |
| stripped coconut sultaine | 2.50 |
| polyoxyethylene (80) sorbitan monolaurate | 5.00 |
| tridecylether sulfate | 5.00 |
| polyvinylpyrrolidine | 2.00 |
| polyethylene glycol 6000 distearate | 1.00 |
| preservative | .10 |
| dye and fragrance | .35 |
| deionized water | q.s. to 100% |
| pH adjusted to 6.5 with dilute HCL. | |

This composition exhibits low irritation and excellent foam properties.

EXAMPLE XVII

A gel detergent composition is prepared having the following formulation:

| | wt./wt. % |
|---|---|
| Compound EE | 10.0 |
| Compound AA | 10.0 |
| triethanolamine lauryl sulfate | 5.0 |
| polyvinylpyrrolidine | 2.0 |
| polyoxyethylene (80) sorbitan monolaurate | 15.0 |
| polyethylene glycol distearate (150) | 3.0 |
| Dowicil 200 | .1 |
| dye and fragrance | .35 |

This composition exhibits low irritation and excellent foam properties.

Various other features and embodiments of the present invention not specifically enumerated will be obvious to those skilled in the art, all of which may be achieved without departing from the spirit and the scope of the invention as defined by the following claims.

What is claimed is:

1. A detergent and cleansing composition wherein the active ingredient consists essentially of from about 1 to 20% by weight of the total composition of a compound selected from the group consisting of a phosphobetaine of the formula $$\left[ R^{\oplus} - Y - O - \overset{\overset{O}{\|}}{\underset{A}{P}} - B \right] X_z^{\ominus} \quad (I)$$

wherein

A is selected from $O^-$, OM, and $-O-Y-R^+$;
B is selected from $O^-$ and $OM'$;
$X^-$ is an anion;
z is an integer from 0 to 2;
with the proviso that only one of A and B can be $O^-$ and z is of a value necessary for charge balance;
R is an amidoamine reactant moiety of the formula $$\left[ R^1 - \overset{\overset{O}{\|}}{C} - \overset{\overset{R^2}{|}}{N} - (CH_2)_n - \overset{\overset{R^3}{|}}{\underset{R^4}{N}} \right]^{\oplus}$$

wherein $R^1$ is alkyl, alkenyl, alkoxy, or hydroxyalkyl of from 5 to 22 carbon atoms each, or aryl or alkaryl of up to 20 carbon atoms;
$R^2$ is hydrogen or alkyl, hydroxyalkyl or alkenyl of up to 6 carbon atoms each or cycloalkyl of up to 6 carbon atoms, or polyoxyalkalene of up to 10 carbon atoms;
$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle structure, in which the Y radical is bonded to a ring atom of said N-heterocycle other than the nitrogen of the R moiety;
n is an integer from 2 to 12;
or R is an N-heterocyclic radical of the formula $$\begin{array}{c} R_6 \\ | \\ N \\ / \phantom{xx} \backslash \\ (CH_2)_o \phantom{xx} (CH_2)_p \\ \backslash \phantom{xx} / \\ Z \end{array}$$

wherein

Z is N, S or O;
o is an integer from 0 to 3;
p is an integer from 1 to 3; provided that the sum of o+p is from 3 to 4;
$R^1$ is defined as before and is linked to a ring carbon atom; and
$R_6$ is alkyl of from 2 to 6 carbon atoms;
Y is alkylene of up to 12 carbon atoms;
M and M', which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals, alkaline earth metals, and mono-, di- or triethanolamine, provided that when either M or M' is an organic radical (b), the other M and M' must be hydrogen or a salt radical (c);

or a phosphitaine of the formula

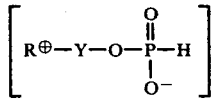

wherein R and Y are as defined above.

2. The composition of claim 1 wherein the phosphobetaine compound is of the formula

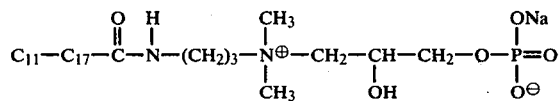

3. The composition of claim 1 wherein the phosphobetaine compound is of the formula

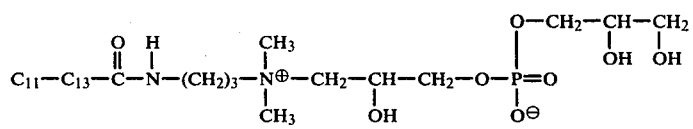

4. The composition of claim 1 wherein the phosphobetaine compound is of the formula

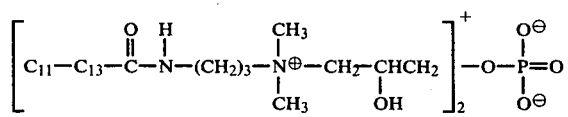

5. The composition of claim 1 wherein the phosphitaine compound is of the formula

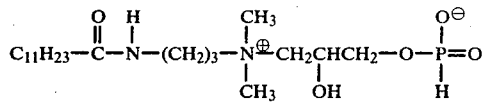

6. The composition of claim 1 wherein the phosphobetaine compound is of the formula

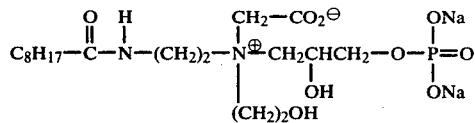

7. The composition of claim 1 containing in addition at least one surfactant selected from the group consisting of anionic, nonionic, cationic and amphoteric surfactants wherein the amphoteric surfactant is selected from the group consisting of betaines, sultaines, n-alkylamino propionates and n-alkylimino dipropionates and wherein the total active level of surfactants shall not exceed 35% by weight of the total composition.

8. The composition of claim 7 containing from about 1 to 20% by weight of the total composition of an anionic surfactant selected from the group consisting of alkylsulfate, alkylether sulfate, alkylmonoglyceryl ether sulfonate, alkylmonoglyceride sulfate, alkylmonoglyceride sulfonate, alkyl sulfonate, alkylaryl sulfonate, alkyl sulfosuccinate, alkyl sarcosinate, acyl isothionate, alkyl methyl tauride, fatty acid protein condensate and an alcohol ether carboxylate.

9. The composition of claim 7 containing from about 1 to 20% by weight of the total composition of a nonionic surfactant selected from the group consisting of alkylene oxide ethers of phenols, mono- or polyhydric alcohols, and alkyl mercaptans; alkylene oxide esters of fatty acid amides; condensation products of ethylene oxide with partial fatty acid esters and mixtures thereof.

10. The composition of claim 7 containing from about 1 to 5% by weight of the total composition of a cationic surfactant selected from the group consisting of mono- and bis-quaternary ammonium halides, tertiary amine salts and cationic polymers.

* * * * *